United States Patent [19]
Hoerrner et al.

[11] Patent Number: 5,932,767
[45] Date of Patent: Aug. 3, 1999

[54] PROCESS FOR PREPARING DIBENZOCYCLOHEPTENE COMPOUNDS

[75] Inventors: Robert S. Hoerrner, Scotch Plains, N.J.; Joseph Auerbach, Brooklyn, N.Y.; John Carolan, Drogheda, Ireland

[73] Assignee: Merck & Co., Inc., Rahway, N.J.

[21] Appl. No.: 08/995,743

[22] Filed: Dec. 22, 1997

Related U.S. Application Data

[60] Provisional application No. 60/034,973, Jan. 6, 1997.
[51] Int. Cl.$^6$ .................................................. C07C 209/38
[52] U.S. Cl. ............................................ 564/376; 564/405
[58] Field of Search ...................... 564/376, 405

[56] References Cited

U.S. PATENT DOCUMENTS

| | | |
|---|---|---|
| 3,383,420 | 5/1968 | Wendler et al. . |
| 3,709,947 | 1/1973 | Cusic .................................. 260/649 R |
| 3,922,305 | 11/1975 | Engelhardt .................... 260/570.8 TC |
| 4,235,820 | 11/1980 | Evans ...................................... 564/427 |

*Primary Examiner*—Brian M. Burn
*Attorney, Agent, or Firm*—Elliott Korsen; Mark R. Daniel

[57] ABSTRACT

Protriptyline can be prepared from 5-dihydrodibenzocycloheptatriene, by deprotonation, followed by reaction at low temperatures with 1,3-bromochloropropane to give the 5-(chloropropyl)-dibenzocycloheptatriene, which is reacted with methylamine in a displacement reaction to give the protriptyline product.

2 Claims, No Drawings

PROCESS FOR PREPARING DIBENZOCYCLOHEPTENE COMPOUNDS

This application claims benefit of Provisional Appln. 60/034,973 filed Jan. 6, 1997.

BACKGROUND OF THE INVENTION

The present invention discloses a method for the preparation of protriptyline by the coupling of dibenzocycloheptatrine with a dihalopropyl group, followed by displacement with methylamine.

Protriptyline, is N-methyl-5H-dibenzo[a,d]-cycloheptene-5-propanamine. The hydrogen chloride salt of protriptyline is used in pharmaceutical preparations as an antidepressant agent. This compound is sold in tablet form under the registered trade name VIVACTIL.

SUMMARY OF THE INVENTION

A method for the preparation of protriptyline is presented comprising the steps of (a) coupling the starting material, dibenzocycloheptatriene, with 1–1.5 equivalents of n-butyl lithium in tetrahydrofuran, at about −25° C. to about 0° C.; (b) adding an approximately equimolar amount of bromochloropropane at about −25° C. to about 0° C.; and (c) aminating the resultant chloro product with an excess of methylamine in the presence of about 50% tetrabutylammonium iodide catalyst at about 50° C. to about 60° C. over about 10 to about 36 hours. The aminating step occurs in 50-50 methanol/toluene solution.

DETAILED DESCRIPTION OF THE INVENTION

The present invention relates to a method of preparing protriptyline by coupling of dibenzocycloheptatriene with a dihalopropyl group, followed by displacement with methylamine. Thus, in accordance with this invention, dibenzocycloheptatrine I

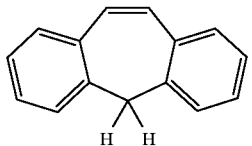

I is contacted with 1–1.5 equivalents of n-BuLi in tetrahydrofuran, aged for 1–4 hours at about −25° C. to about 0° C., then added to an approximately equimolar amount of bromochloropropane at about −25° C. to about 0° C. The compound of the following structure is produced,

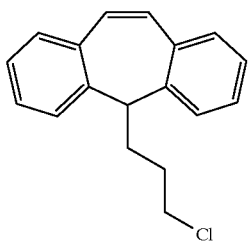

II which is aminated in a displacement reaction using a 1 M solution of the chloride (of Formula II) in methanol/toluene, with about 50% tetrabutyl-ammonium iodide catalyst and an excess of methylamine, at about 50° C. to about 60° C. over 10–36 hours. The conversion is above 95%. The product is crude protriptyline, isolated from toluene as the hydrochloride salt.

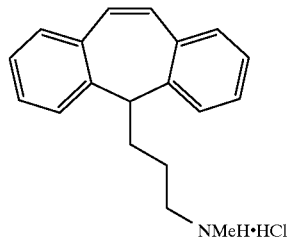

III

Compound III can be recrystallized using standard procedures to yield the pure protriptyline.

Protriptyline is commercially available and is useful as an antidepressant. A U.S. Patent relating to this product is U.S. Pat. No. 3,922,305; related process chemistry is disclosed in U.S. Pat. No. 4,235,820, both assigned to Merck & Co., Inc.

The process of this invention is described in the following examples.

All reagents were commercial quality from freshly opened containers. The starting material (A) Trienone was purchased commercially and used without further purification. n-Butyl lithium, tetrahydrofuran, 1-bromo-3-chloropropane and 1,3-dibromopropane were purchased from Aldrich. Tetrahydrofuran was dried using 4 Å molecular sieves. Methylamine gas was purchased from Matheson. The concentration of n-butyl lithium was determined by titration with 1,2 dibromoethane. N.M.R. spectra were recorded on a Varian, Gemini 200 MHz instrument.

EXAMPLE 1

5-Hydroxy dibenzocycloheptatriene (A)

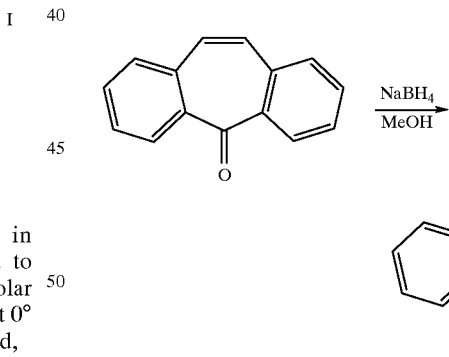

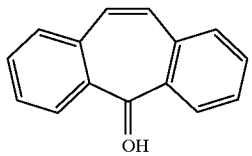

Trienone (206.2 g, 1 mole) is dissolved in 1.4 liters of methanol and sodium borohydride (19 g, 0.5 moles) in 140 ml water, containing sodium hydroxide (0.15 g, 0.004 moles). The batch is allowed to rise to a maximum of 60° C. during the borohydride addition and then the batch is heated at reflux temperature (72° C.) for 0.5 hours. (Note the reaction is run under a blanket of nitrogen). The batch is diluted with 75 mls of toluene and then is added to 1.3 liters of cold water maintaining the temperature during this operation at 20° C. or below. The batch is diluted with 0.8 liters water and cooled to about 5° C. to about 10° C. The product alcohol, is removed by filtration, washed with 0.8 liters water and dried at 60° C. The yield is 90–100%.

EXAMPLE 2

5-Dihydrodibenzocycloheptatriene (I)

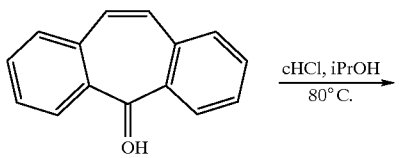

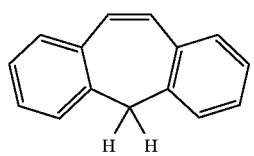

To a solution of isopropanol (281 ml) at 0° C. is added concentrated HCl (12 ml) over 10–15 minutes. The reaction mixture is allowed to warm to 10° C. during the addition. The trienol (30 g) is added over 15 minutes at 10° C. (note: most of the solids remained out of solution). The batch is gradually heated to 82° C. (reflux) over one hour. The batch is aged at 82° C. for 2–4 hours until judged complete by TLC. Deionized water (70 ml) is added dropwise over one hour at 80° C. (note: batch began to crystallize after 10 ml water addition). The batch is allowed to slowly cool to 0° C. over 6–8 hours. The batch is aged at 0° C. for one hour and The product solid is washed with 50 ml (1:1 IPA/water). The solid is vacuum dried at about 50–60° C. and 25 mmHg to provide 24.8 g (88.4% yield).

EXAMPLE 3

Procedure for n-Butyl Lithium Preparation of 5-(chloropropyl)-Dibenzocycloheptatriene (1.2 eq.)

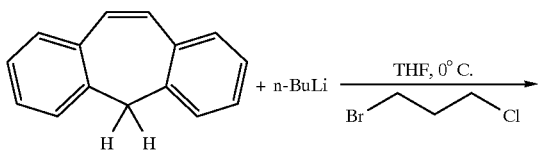

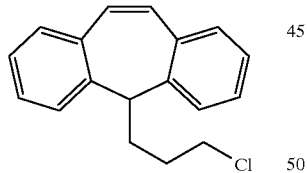

To a solution of dibenzocycloheptatriene (7.2 g) in dry THF (50 ml) at 0° C. is added n-butyl lithium (30 ml, 1.6 M in hexane) over 15 minutes. The reaction is aged at 0° C. for 60 minutes. A separate solution of bromochloropropane (one mole equivalent to starting material) in dry THF (50 ml) is prepared and cooled to about −15° C. The lithium anion solution is added to the bromochloropropane solution over 90 minutes maintaining the temperature at about −15° C. The reaction is aged at about −15° C. for 60 minutes and allowed to warm to about 0° C. over 60 minutes. Upon completion of the reaction, which is detected by HPLC, a deionized water charge (15 ml) is made and the layers agitated for 15 minutes. The water layer is separated, the organic layer is dried with magnesium sulfate and evaporated to dryness under vacuum (15–20 mmHg, 30–40° C.).

The oil is separated on a silica gel column using a mobile phase of 5% ethyl acetate/hexane. Yield of 5-(chloropropyl)-dibenzocycloheptatriene was 80%.

EXAMPLE 4

Preparation of 5-(N-methyl-aminopropyl) dibenzocycloheptatriene from 5-(chloropropyl)-dibenzocycloheptatriene

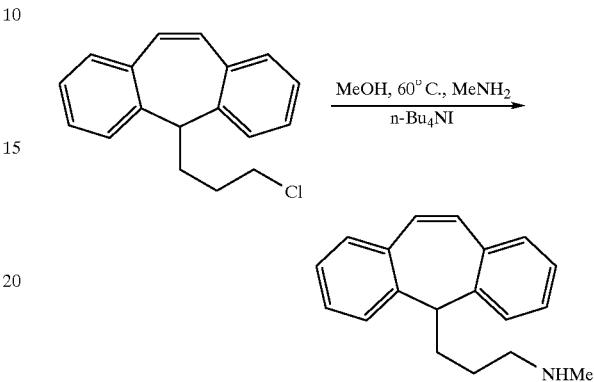

Methylamine (g) is condensed at −10° C. to provide 4–5 ml of liquid methylamine. A solution of tetrabutyl ammonium iodide (0.7 g) in methanol (2.5 ml) is added to the methylamine at 10° C. The chloropropyl compound is dissolved in methanol (1.0 ml) and toluene (0.5 ml) and is added over 5 minutes to the methylamine solution. The reaction mixture is heated to about 50° C. to about 60° C. and aged for 24 hours. The batch mixture is diluted with 50 ml toluene and extracted with deionized water (three times with 10 ml) and once with brine (10 ml). A charge of concentrated HCl (0.34 mL) is made and the toluene solution is concentrated to 40 ml under vacuum (15 mmHg, 70–80° C.) to remove the water. The batch is cooled to about 0° C. and the solids are isolated by filtration. The solids are washed with 5 ml cold toluene. The product, crude protriptyline HCl, is dried under vacuum (25 mmHg, 50° C.) to provide 0.8 g material.

EXAMPLE 5

Purification Step

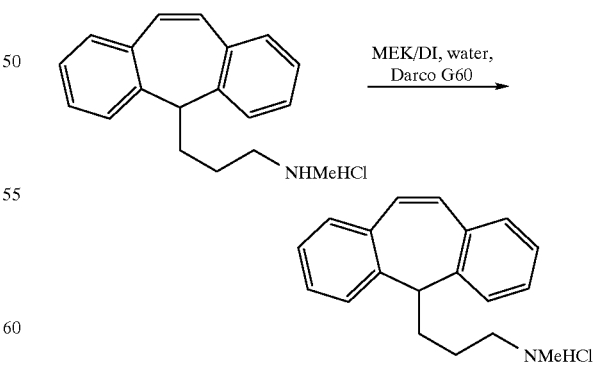

A 3-necked round bottomed flask with a heating mantle, stirrer, condenser and nitrogen purge were used to perform this step of the synthesis. An erlenmeyer flask was charged with 608.5 ml methyl ethyl ketone and 14.8 ml of water. A moisture determination of the solution, using the Karl Fisher method, should be 2.9–3.1%. A buchner funnel was pre-coated with 0.42 g of filter aid in MEK and the filtrate was discarded. A charge of 434.6 ml of MEK/water and 52.08 g of protriptyline crude were charged to a round bottomed flask with 2.60 g of Darco G60 and 0.31 g filter aid. The batch was heated at about 75° C. to about 77° C. and aged for 30 minutes to insure that all the protriptyline was in solution. The batch was filtered through the heated precoated buchner funnel. The round bottomed flask and cake were washed with 86.93 ml hot (75° C.) MEK/water. A three necked round bottom flask was set up for an atmospheric distillation. The hot filtrate was charged and distilled until a thick slurry was obtained. 130.4 ml of MEK was charged to the pot and distilled again to a thick slurry. The concentration of water in the slurry was determined using the Karl Fisher method. If the Kf is less than 0.3%, the distillation must be repeated. The batch was cooled to about 20° C. to about 25° C. and aged for 2 hours. The batch was filtered and washed with 52.2 ml of MEK and cooled to about 2° C. to 5° C. The protriptyline pure cake was dried at 50° C. under vacuum to an LOD of less than 0.10%.

What is claimed is:

1. A process for preparing protriptyline comprising the steps of:
    (a) contacting the starting material, dibenzocycloheptatriene, with 1–1.5 equivalents of n-butyllithium in tetrahydrofuran, at about −25° C. to about 0° C.;
    (b) adding an approximately equimolar amount of bromochloropropane at about −25° C. to about 0° C.; and
    (c) aminating the resultant chloro product with an excess of methylamine in the presence of about 50% tetrabutylammonium iodide catalyst at about 50° C. to about 60° C. over 10–36 hours.

2. The process of claim 1 in which the aminating step takes place in 50—50 methanol/toluene solution.

* * * * *